(12) United States Patent
Krupa et al.

(10) Patent No.: US 8,668,682 B2
(45) Date of Patent: Mar. 11, 2014

(54) VACUUM REGULATORS WITH VAP FEATURES

(75) Inventors: Michael Andrew Krupa, Northampton, PA (US); Jeremy Charnegie, Emmaus, PA (US)

(73) Assignee: Precision Medical, Inc., Northampton, PA (US)

( * ) Notice: Subject to any disclaimer, the term of this patent is extended or adjusted under 35 U.S.C. 154(b) by 695 days.

(21) Appl. No.: 12/779,776

(22) Filed: May 13, 2010

(65) Prior Publication Data

US 2011/0282326 A1  Nov. 17, 2011

(51) Int. Cl.
*A61M 1/00* (2006.01)
(52) U.S. Cl.
USPC .................................... 604/540; 604/319
(58) Field of Classification Search
USPC ............... 604/93.01, 131, 317, 319, 540
See application file for complete search history.

(56) References Cited

U.S. PATENT DOCUMENTS 3,731,691 A * 5/1973 Chen ..................... 128/207.15
6,599,269 B1 * 7/2003 Lewandowski et al. ...... 604/110

OTHER PUBLICATIONS

Manzanet, G. MD, PhD, A Hydrodynamic Study of Pleural Drainage Systems. Chest 2005; 127:2211-2221.*

* cited by examiner

*Primary Examiner* — Melanie Hand
(74) *Attorney, Agent, or Firm* — Akerman LLP; Richard P. Gilly

(57) ABSTRACT

A vacuum regulator apparatus for continuous subglottic aspiration is provided. In one version, the regulator apparatus attaches to a standard vacuum regulator and shares the same vacuum supply outlet as the standard vacuum regulator. Sufficient airflow is provided through the regulator apparatus and calibrated bleed orifice to provide proper continuous subglottic aspiration. Vacuum levels to maintain the airflow are in a range suitable to provide patient comfort. A ball flow indicator provides visual indication of flow through a subglottic tube interface port of the regulator apparatus. A direct flow channel can be momentarily opened causing flow to bypass the regulator module in for clearing blockages affecting the subglottic tube interface port.

22 Claims, 6 Drawing Sheets

VACUUM REGULATORS WITH VAP FEATURES

FIELD

The present disclosure relates to hospital vacuum regulators and in particular to vacuum regulator apparatus for controlling airflow related to removal of secretions from patient airways.

BACKGROUND

Hospital acquired infections such as ventilator-associated pneumonia (VAP) are a serious medical concern and a leading cause of death among hospital patients. Such infections often are caused by aspiration of oral or gastric secretions which can convey harmful bacteria to a patient's lungs. Subglottic secretions which accumulate above an endotracheal tube cuff are a major source of infection in mechanically ventilated patients.

It is often desirable to institute continuous aspiration of subglottic secretions using a specialized endotracheal tube with separate dorsal suction lumen to remove oral and/or gastric secretions from above the endotracheal tube cuff before they are aspirated. An illustrative embodiment of an endotracheal tube having a subglottic evacuation lumen is described with reference to FIG. 1. The endotracheal tube 100 includes a ventilator tube portion 102, a cuff 104 and a cuff inflation valve 106 for inflating the cuff 104. A subglottic tube 108 includes suction lumen 109 incorporated with the endotracheal tube 100 for continuous aspiration of subglottic secretions through an evacuation port 110 above the cuff 104.

Vacuum is often applied to the subglottic tube through a standard hospital vacuum regulator. However, the use of standard hospital vacuum regulators is accompanied by drawbacks and disadvantages. In general terms, use of current vacuum regulators does not generally yield adequate flow of air at the typical range of vacuum levels associated with such devices.

Standard hospital vacuum regulators also do not typically include flow indicators suitable for recognizing blockage of the subglottic tube. Medical personnel often visually check the subglottic tube for small amounts of secretions every few hours. If blockages are suspected, the medical personnel are generally required to disconnect the subglottic tube from the standard hospital regulator and administer a bolus of air to the tube using a syringe, for example. Each disconnection and reconnection of the subglottic tube greatly increases the chances of bacterial contamination leading to dangerous infection.

Also, disadvantageously, the use of a standard hospital vacuum regulator for subglottic aspiration reduces the availability of vacuum sources for various other suction procedures that are often necessary. The use of a standard hospital vacuum regulator also takes up available space between other gas supply outlets (i.e. oxygen, air) which is typically limited in a hospital environment.

SUMMARY

Illustrative embodiments provide a vacuum regulator apparatus for continuous subglottic aspiration. In one version, the regulator apparatus attaches to a standard vacuum regulator and shares the same vacuum supply outlet as the standard vacuum regulator. Sufficient airflow is provided through the regulator apparatus to provide a more effective level of continuous subglottic aspiration. Vacuum levels to maintain the airflow are in a range suitable to provide patient comfort. A ball flow indicator provides visual indication of flow through a subglottic tube interface port of the regulator apparatus. A direct flow channel can be momentarily opened causing flow to bypass the regulator module for clearing blockages affecting the subglottic tube interface port.

A vacuum regulator apparatus as disclosed herein may be designed to yield flow rates greater than about 20 liters per minute (LPM) at vacuum levels of about 20 mm Hg to about 30 mmHg. This can be accomplished with a small diaphragm of about 0.750" diameter in the regulator module by introducing a calibrated bleed which allows the regulator to pull further away from the orifice, creating higher flows at low vacuum levels.

The vacuum regulator apparatus may include an internal vacuum flow channel, a vacuum source port in communication with the internal vacuum flow channel, and a subglottic tube interface port in communication with the internal vacuum flow channel. A regulator module is arranged in communication with the internal vacuum flow channel and disposed between the vacuum source port and the subglottic tube interface port. An orifice to ambient pressure is provided in communication with the internal vacuum flow channel between the regulator module and the subglottic tube interface port. The orifice is configured to provide increased flow through the subglottic tube interface port for a selected vacuum.

In some versions of the vacuum regulator apparatus, the vacuum source port is configured for a piggyback connection to a facility vacuum supply along with at least one other vacuum device. A flow indicator ball is disposed in communication with the subglottic tube interface port. The flow indicator ball is visibly held in an elevated position by an airflow from a subglottic tube through the subglottic tube interface port and visually indicates that flow is occurring to move subglottic secretions collecting above to endotracheal tube cuff. If flow in the subglottic tube becomes blocked or clogged, the ball would fall into the no flow area. The indicator ball is configured to be held in the elevated position when said airflow is sufficient for proper subglottic aspiration.

Illustratively, a normally closed direct flow channel is provided between the vacuum source port and the subglottic tube interface port. A momentary actuator such as a spring biased push button valve, for example, is configured to open the direct flow channel causing flow to bypass the regulator module in response to a momentary manipulation by a user for clearing blockages affecting the subglottic tube interface port.

In yet another illustrated version, the subglottic tube vacuum regulator includes an internal vacuum flow channel, a subglottic tube interface port in communication with the internal vacuum flow channel, and a bleed orifice in the internal vacuum flow channel to provide increased flow through the subglottic tube interface port for a reduced vacuum in the internal vacuum flow channel. A flow indicator ball is provided in communication with the subglottic tube interface port. The flow indicator ball is configured to be visibly held in an elevated position by airflow through the subglottic tube interface port.

A method for improved subglottic aspiration to a medical patient is disclosed. The method includes the steps of connecting a regulator apparatus between a facility vacuum supply and a subglottic tube being used on the medical patient. Vacuum is applied through a vacuum source port in communication with an internal vacuum flow channel. Vacuum is selectively controlled through a regulator module in communication with the internal vacuum flow channel. External air is bled through an orifice into the internal vacuum flow channel between the regulator module and a subglottic tube interface port subglottic to provide increased flow through the subglottic tube interface port for a selected vacuum.

BRIEF DESCRIPTION OF THE DRAWINGS

The foregoing and other features and advantages of the present disclosure will be more fully understood from the following detailed description of illustrative embodiments, taken in conjunction with the accompanying drawings in which.

DETAILED DESCRIPTION OF THE DRAWINGS

Figure 1:
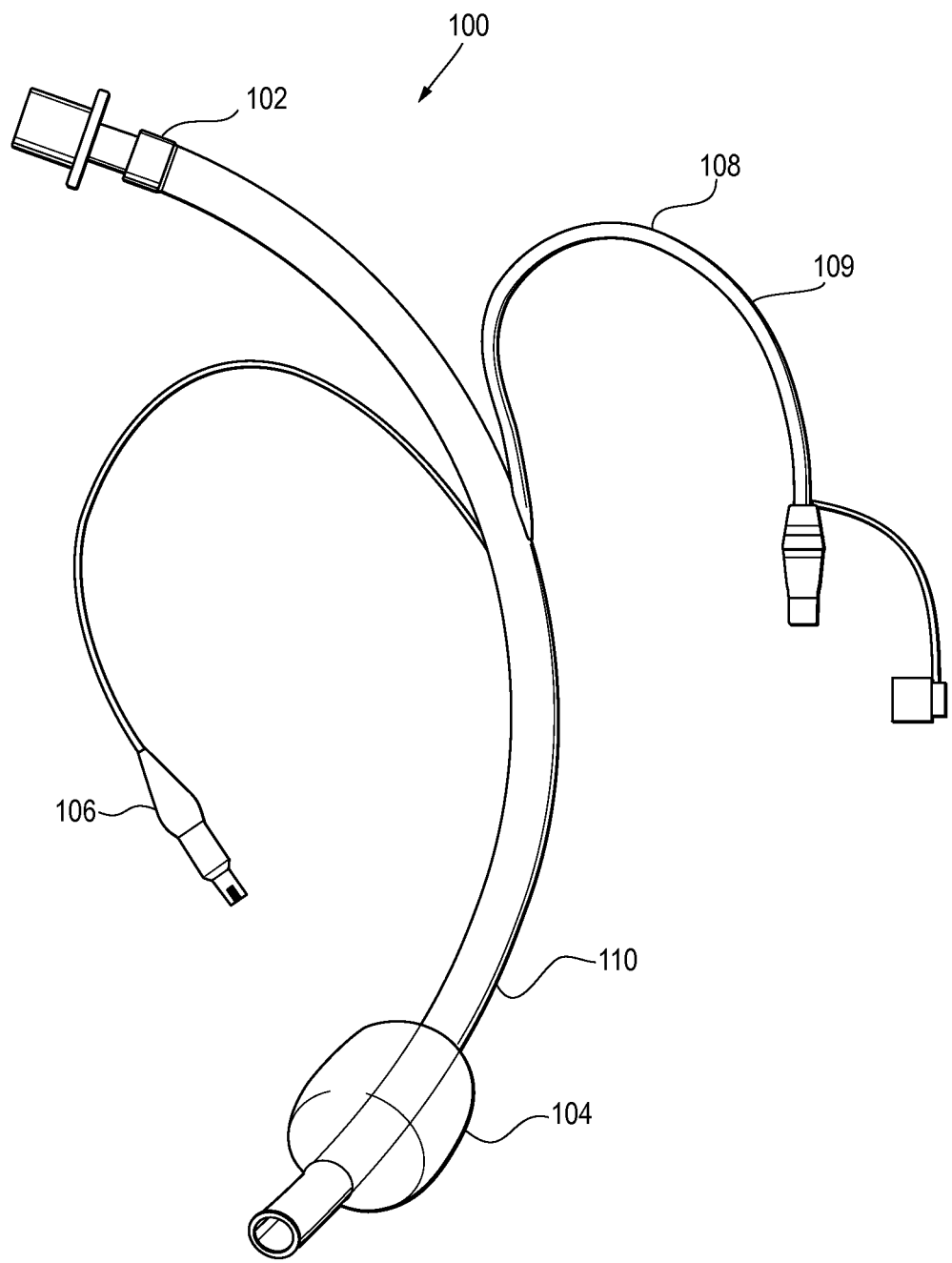
FIG. 1 is a plan view of an endotracheal tube with separate dorsal suction lumen for continuous aspiration of subglottic secretions according to the prior art.
Figure 2:
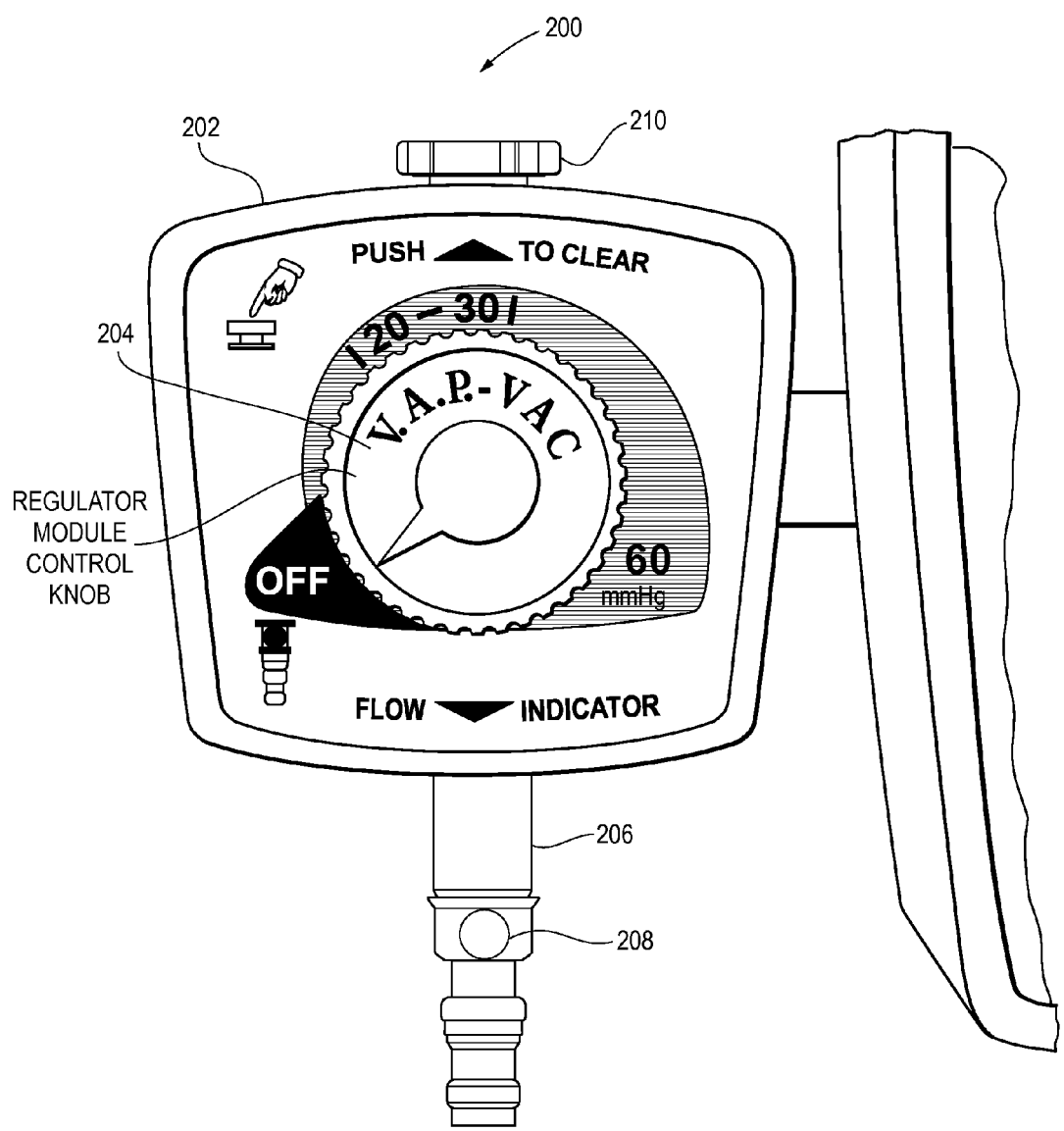
FIG. 2 is a front plan view of one implementation of a vacuum regulator apparatus according to the disclosure.

Turning to the drawings, one implementation of vacuum regulator apparatus according to the present disclosure is described with reference to FIGS. 2 and 3. Regulator apparatus 200 includes a body 202 and a regulator module control knob 204 for adjusting vacuum pressure in a range from about 0 mm Hg to about 60 mm Hg. A subglottic tube interface port 206 extends downward from the body 202 and includes a flow indicator ball 208 disposed therein. A "push-to-clear" button 210 extends upwardly from the body 210.

Figure 3:
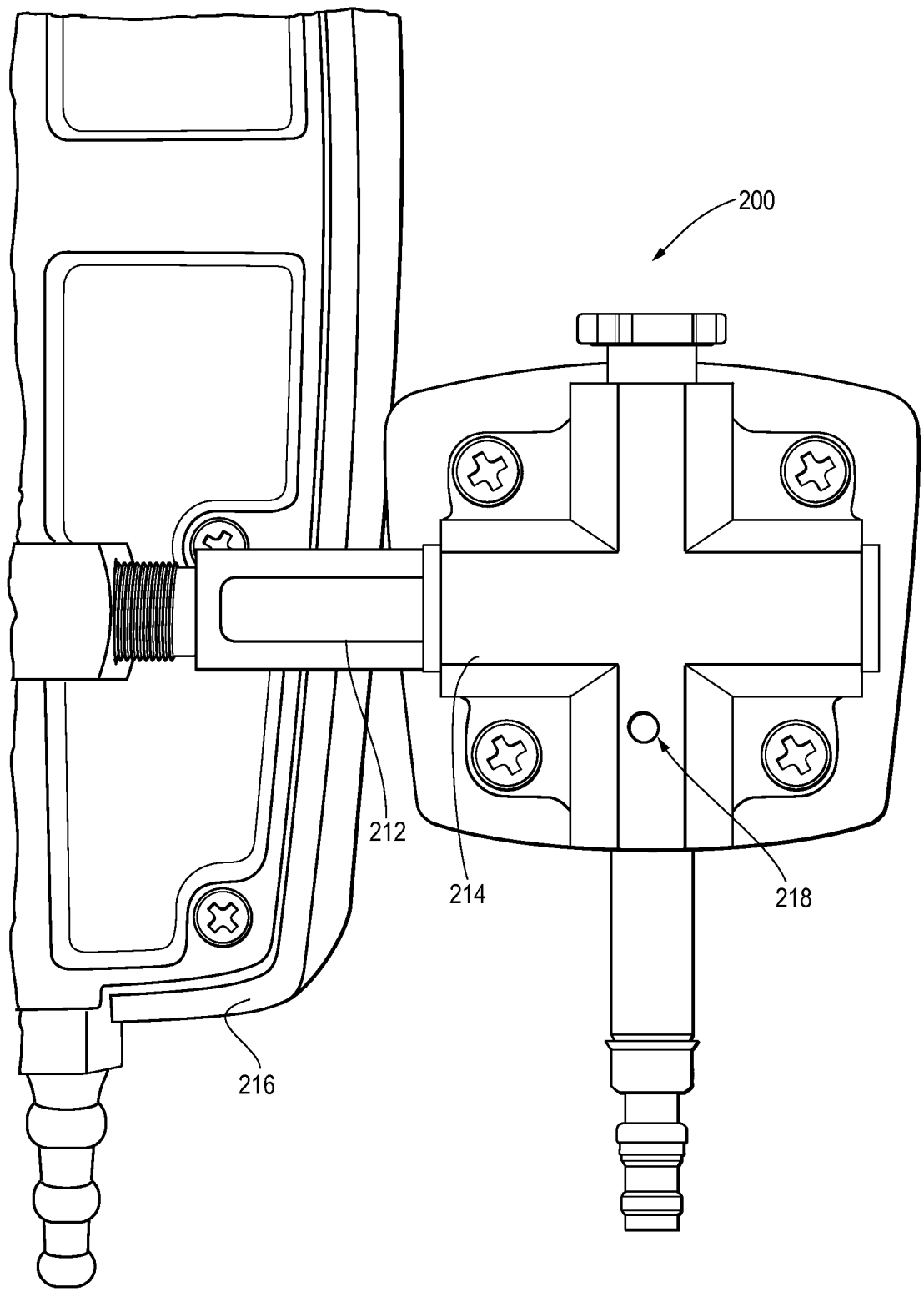
FIG. 3 is a rear plan view of the vacuum regulator apparatus of FIG. 1.

FIG. 3 provides a rear view of the illustrative vacuum regulator apparatus. A vacuum source fitting 212 extends horizontally from a vacuum source port 214. The vacuum source fitting 212 is connectable to a facility vacuum source along with a standard hospital vacuum regulator 216. The version shown in FIG. 3 is attached in a piggyback configuration to the standard hospital vacuum regulator 216 and shares the same vacuum outlet with the standard hospital vacuum regulator 216. A filter with a bleed orifice 218 is disposed in the rear of the body 202. The size of bleed orifice 218 is selected or calibrated to improve the flow rate of air associated with a given vacuum level, as explained subsequently.

Figure 4:
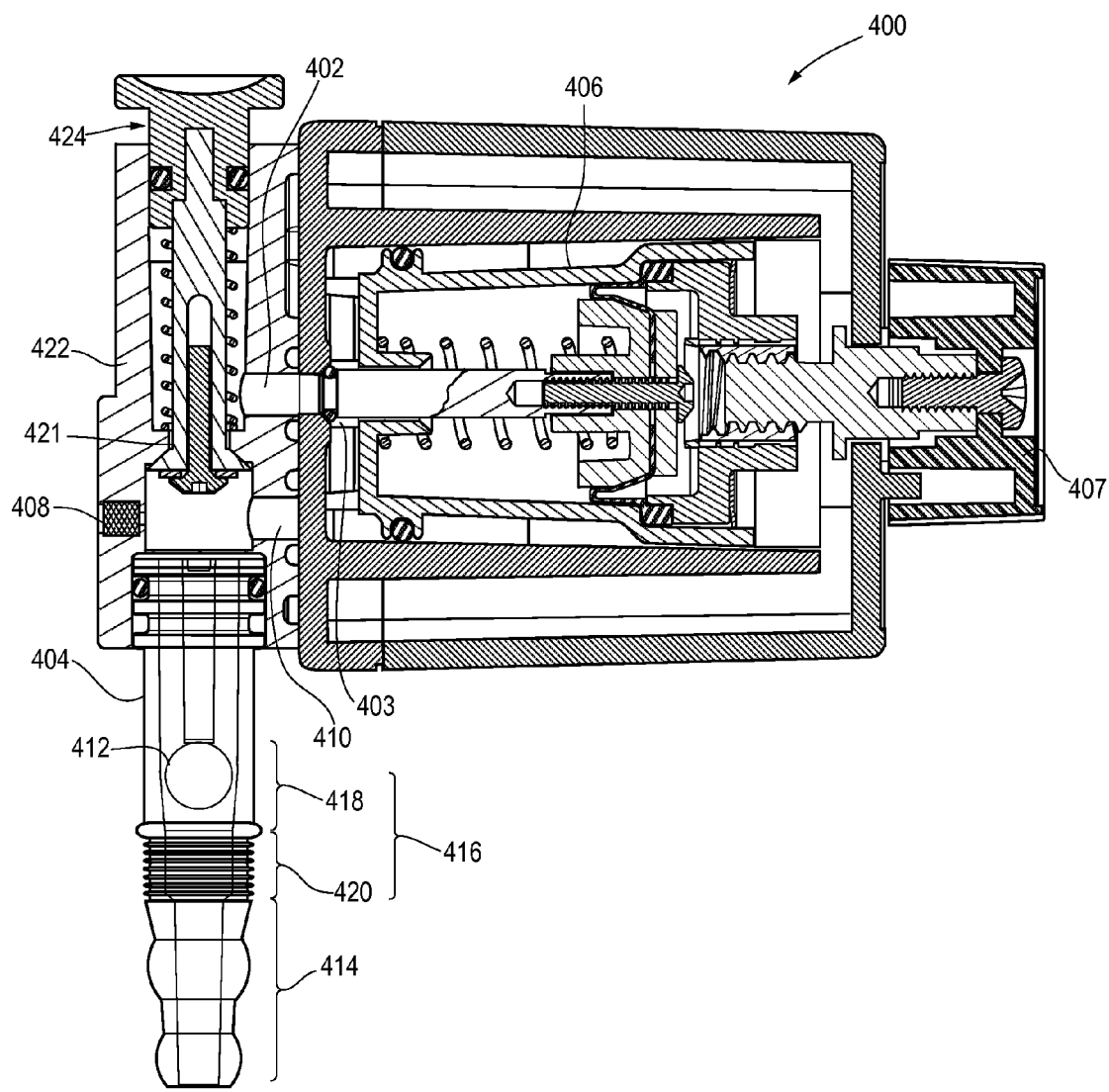
FIG. 4 is a cross sectional view of another implementation of a vacuum regulator apparatus according to the disclosure.

FIG. 4 is a cross-sectional view of another possible implementation of the vacuum regulator apparatus disclosed herein. The vacuum regulator apparatus 400 includes an internal vacuum flow channel 402 in communication with the vacuum source port (shown in FIG. 3 and FIG. 5). In the illustrative embodiment, the diameter of the vacuum flow channel 402 is preferably about 0.093 inches when the regulator diaphragm is 0.75 inches. A subglottic tube interface port 404 is configured in communication with the internal vacuum flow channel 402. A regulator module 406 is arranged in communication with the internal vacuum flow channel 402 and disposed between the vacuum source port and the subglottic tube interface port 404. A control knob 407 is configured for manual adjustment of the regulator module 406. In this version, the control knob 407 is rotatable from an off position through about 270 degrees of rotation to a full open position to provide about 75 mm Hg.

An orifice 408 to ambient pressure is provided in communication with the internal vacuum flow channel 402 between the regulator module 406 and the subglottic tube interface port 404. The orifice 408 and regulator module 406 are selected to provide desired flow rates at comparatively low vacuum levels through a regulated supply port 410. In an illustrative embodiment, the orifice has a diameter of about between 0.039 inches and 0.045 inches. In one implementation, regulator module 406 has a diaphragm of a diameter generally smaller than those of standard vacuum regulators, and orifice 408 is calibrated so that flow ranges between about 20 liters per minute to about 60 liters per minute. In at least one preferred the regulator module eludes an o-ring 403 in communication with the vacuum flow channel 402. A smaller-diameter diaphragm of regulator module 406, such as 0.75" in one preferred implementation, along with the vacuum flow channel 402 having about 0.093 inches, and an o-ring 403, such as a 2-002 Parker o-ring size, for example, allows proper subglottic flow and vacuum levels. Due in part to the smaller diaphragm diameter, this configuration also allows apparatus 400 to be more compact and fit into confined environments more easily.

A flow indicator, such as flow indicator ball 412, is disposed in communication with the subglottic tube interface port 404. The subglottic tube interface port 404 includes an inlet connection 414 for attaching to the subglottic tube. The flow indicator ball 412 is visibly held in an elevated position by an airflow from a subglottic tube through the subglottic tube interface port 404 and visually indicates that flow is occurring to move patient secretions, such as subglottic secretions collecting above an endotracheal tube cuff.

In the version illustrated in FIG. 4, the subglottic tube interface port 404 also includes flow indicator portion 416 having a 'FLOW' position 418 and a 'NO FLOW' position 420. Flow through the subglottic tube interface port 404 is indicated if ball 412 rises or is maintained in the 'FLOW' position 418. An indicator ball 412 falling or being maintained in the 'NO FLOW' position indicates that the vacuum regulator apparatus 400 is turned off at the control knob, 407, or that the subglottic tube may be blocked. Other types of flow indicators are likewise contemplated, including visually and audibly perceptible types.

Any of the foregoing variations of vacuum regulator apparatus disclosed herein may be equipped with a direct flow channel, such as shown by reference 421 of FIG. 4. In this version, direct flow channel 421 extends between a vacuum source port, such as port 214 (FIG. 2), and the subglottic tube interface port 404. Flow channel 421 is closed during the typical continuous aspiration cycle discussed herein. In this case a spring-biased, movable seal is provided. A momentary actuator, such as a spring biased push button valve 422 having a "push-to-clear button 424, for example, is configured to open direct flow channel 421, causing flow to bypass the regulator module 406 in response to a momentary manipulation by a user for clearing blockages affecting the subglottic tube interface port 404. In this way, blockages can be cleared out having to disconnect the subglottic tube from its port and thus avoiding possible sources of contamination.

Figure 5:
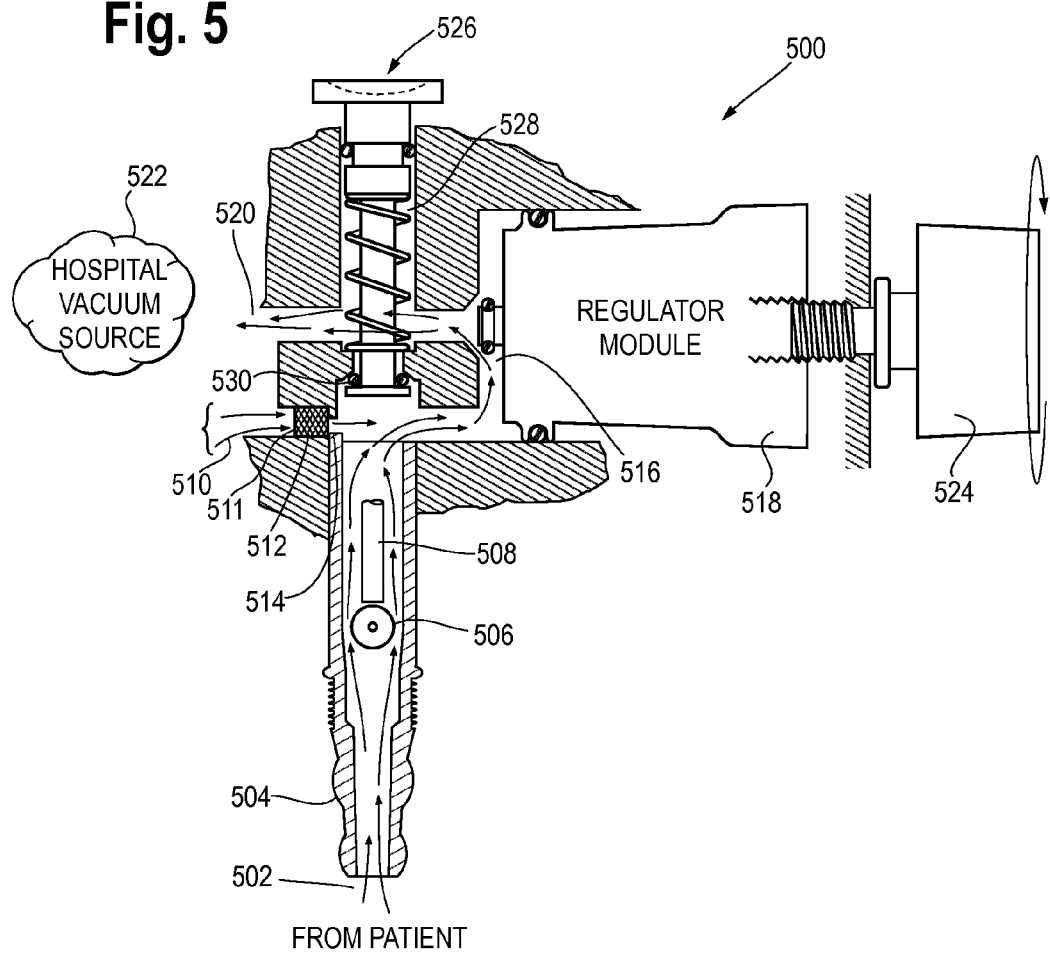
FIG. 5 is a flow diagram showing flow through a vacuum regulator apparatus according to the disclosure.

One possible configuration of airflow is described with reference to FIG. 5 and a vacuum regulator apparatus 500 according to the present disclosure. Negative airflow out of a patient, that is, vacuum, travels through the subglottic tube interface port 504 holding the indicator ball 506 in an elevated position (FLOW position) against a stop 508. Flow travels around the stop 506 where it mixes with bleed air 510 being pulled from the ambient atmosphere through a filter 511 and calibrated bleed orifice 512. The presence of orifice 512 creates a flow rate higher than would have been otherwise associated with the setting of vacuum regulator 518.

The combined flow from the patient and from the bleed orifice travels through a regulated path 516, which path is adjustable by the regulator module 518 and ultimately through the vacuum supply port 520 to a hospital vacuum source 522. Rotation of the regulator module control knob 524 retracts or advances a control portion of regulator module 518 to respectively increase or decrease the effective size or cross section of regulated path 516 to the vacuum source to control vacuum level.

Figure 6:
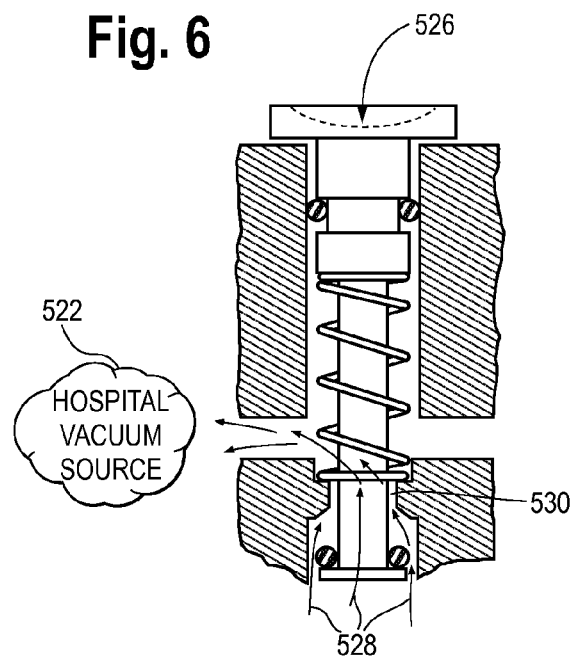
FIG. 6 is a flow diagram showing flow through a bypass valve to bypass the vacuum regulator for clearing a blockage according an illustrative embodiment of the invention.

The "push-to-clear" button 526 is biased in the normally closed position by spring 528 which holds a bypass valve 530 closed against a sealing surface and prevents flow through a bypass flow path (best seen in FIG. 6). In FIG. 6, the "push-to-clear" button 526 is shown in the actuated state in which the button 526 is pushed down to clear a blockage in the subglottic tube, for example. Airflow 528 including flow from the subglottic tube interface port mixed with bleed air from the bleed orifice bypass the regulated path 516 and travels through bypass flow path 530 to the hospital vacuum source 522.

Figure 7:
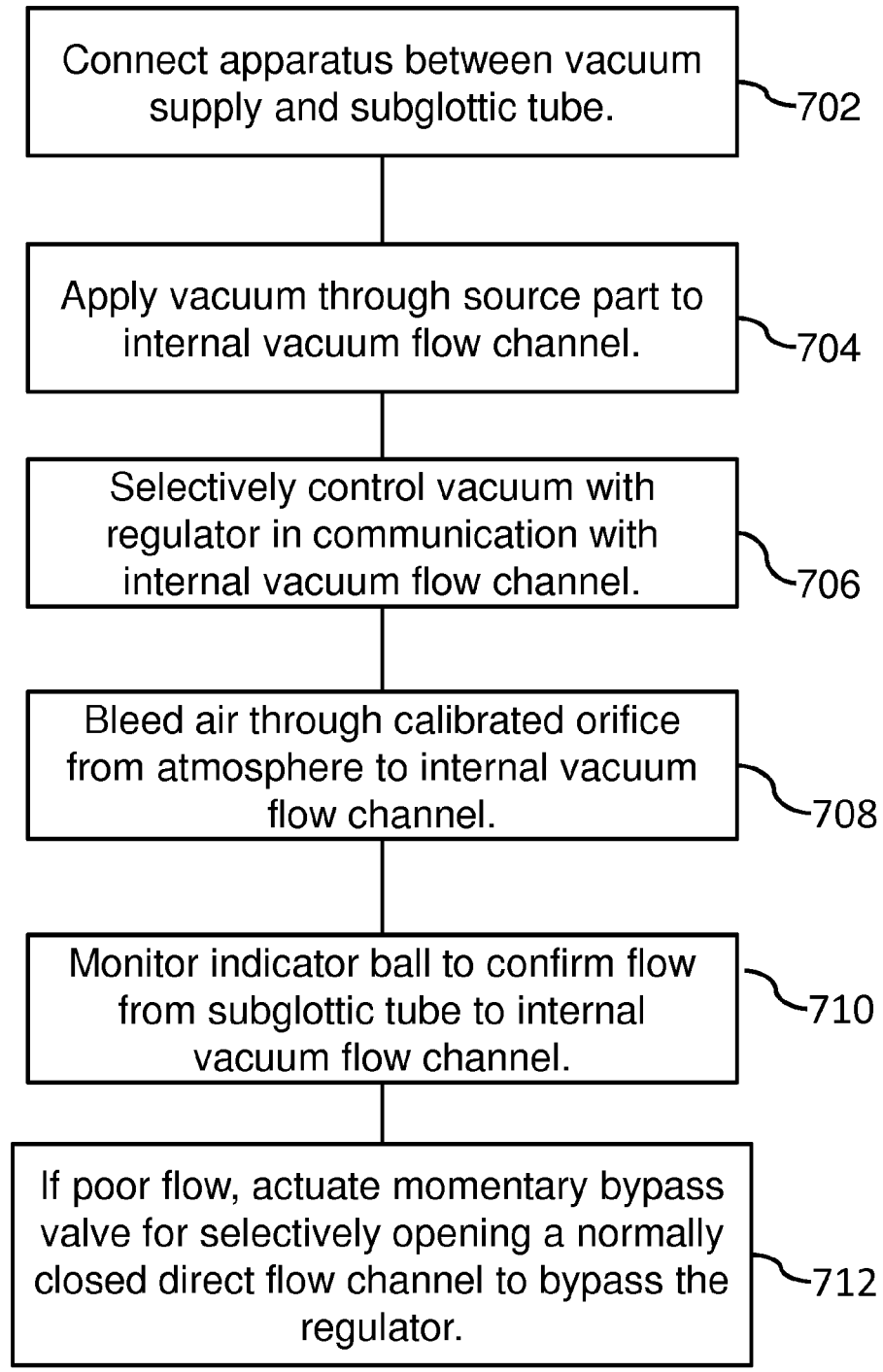
FIG. 7 is a process flow diagram showing a method for improved subglottic aspiration to a medical patient according to an illustrative embodiment of the invention.

A method for improved subglottic aspiration to a medical patient according to an illustrative embodiment of the invention is described with reference to FIG. 7. The method 700 includes the steps of connecting a regulator apparatus between a facility vacuum supply and a subglottic tube being used on the medical patient 702. Vacuum is applied through a vacuum source port in communication with an internal vacuum flow channel 704. Vacuum is selectively controlled through a regulator module in communication with the internal vacuum flow channel 706. External air is bled through an orifice into the internal vacuum flow channel between the regulator module and a subglottic tube interface port subglottic to provide increased flow through the subglottic tube interface port for a selected vacuum 708. Flow in the subglottic tube interface port can be adjusted to about between 20 and 40 liters per minute for a corresponding selected vacuum of about between 30 and 60 mmHg.

In some implementations, the method includes monitoring a flow indicator ball in communication with the subglottic tube interface port to confirm that the flow indicator ball is visibly held in an elevated position by an airflow from a subglottic tube through the subglottic tube interface port 710. Illustratively, the indicator ball is configured to be held in the elevated position when the airflow is sufficient for proper subglottic aspiration.

In still other implementations, the method includes opening a normally closed direct flow channel between the vacuum source port and the subglottic tube interface port 712. The method includes actuating a momentary actuator such as a spring biased push button valve, for example, to open the direct flow channel causing flow to bypass the regulator module in response to a momentary manipulation by a user for clearing blockages affecting the subglottic tube interface port.

While the invention has been described with reference to illustrative embodiments, it will be understood by those skilled in the art that various other changes, omissions and/or additions may be made and substantial equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A vacuum regulator apparatus, comprising:
   an internal vacuum flow channel;
   a vacuum source port in communication with the internal vacuum flow channel;
   a subglottic tube interface port in communication with the internal vacuum flow channel;
   a regulator module in communication with the internal vacuum flow channel; and
   an orifice to ambient pressure in communication with the internal vacuum flow channel, wherein the orifice is configured to provide increased flow through the subglottic tube interface port for a selected vacuum.

2. The vacuum regulator apparatus of claim 1, wherein the vacuum source port is configured for a piggyback connection to a facility vacuum supply along with at least one other vacuum device.

3. The vacuum regulator apparatus of claim 1, wherein the increased flow is between about 20 and about 40 liters per minute for a corresponding selected vacuum of between about 20 and about 60 mmHg.

4. The vacuum regulator apparatus of claim 1, wherein the orifice has a diameter of about between 0.039 inches and 0.045 inches.

5. The vacuum regulator apparatus of claim 1, comprising:
   a flow indicator ball disposed in communication with the subglottic tube interface port, wherein the flow indicator ball is visibly held in an elevated position by an airflow from a subglottic tube through the subglottic tube interface port.

6. The vacuum regulator apparatus of claim 5, wherein the indicator ball is configured to be held in the elevated position when said airflow is sufficient for proper subglottic aspiration.

7. The vacuum regulator apparatus of claim 1, comprising:
   a direct flow channel between the vacuum source port and the subglottic tube interface port;
   wherein the direct flow channel is normally closed; and
   a momentary actuator in communication with the direct flow channel, the momentary actuator configured to open the direct flow channel causing flow to bypass the regulator module in response to a momentary manipulation by a user for clearing blockages affecting the subglottic tube interface port.

8. The vacuum regulator apparatus of claim 7, wherein the momentary actuator comprises a spring biased push button valve.

9. A vacuum regulator apparatus, comprising:
   a vacuum source port in communication with an internal vacuum flow channel;
   a subglottic tube interface port in communication with the internal vacuum flow channel;
   a regulator module in communication with the internal vacuum flow channel, the regulator module selectively reducing vacuum to the subglottic tube interface port;
   an orifice to ambient pressure in communication with the internal vacuum flow channel, wherein the orifice is configured to increase flow to the subglottic tube interface port for a selected vacuum;

a flow indicator ball disposed in communication with the subglottic tube interface port, wherein the flow indicator ball is visibly held in an elevated position by an airflow from a subglottic tube through the subglottic tube interface port;

a direct flow channel between the vacuum source port and the subglottic tube interface port; wherein the direct flow channel is normally closed; and a momentary actuator in communication with the direct flow channel, the momentary actuator configured to open the direct flow channel causing flow to bypass the regulator module in response to a momentary manipulation by a user for clearing blockages affecting the subglottic tube interface port.

10. The apparatus of claim 9, wherein the vacuum source port is configured for a piggyback connection to a facility vacuum supply along with at least one other vacuum device.

11. A method for providing improved subglottic aspiration to a medical patient, comprising:

connecting a regulator apparatus between a facility vacuum supply and a subglottic tube being used on the medical patient;

applying vacuum through a vacuum source port in communication with an internal vacuum flow channel;

selectively controlling vacuum through a regulator module in communication with the internal vacuum flow channel; and bleeding external air through an orifice into the internal vacuum flow channel to provide increased flow through the subglottic tube interface port for a selected vacuum.

12. The method of claim 11, comprising:

configuring the vacuum source port in a piggyback connection to the facility vacuum supply along with at least one other vacuum device.

13. The method of claim 11, comprising:

reducing the flow in the subglottic tube interface port to between about 20 and about 40 liters per minute for a corresponding selected vacuum of between about 20 and about 60 mmHg.

14. The method of claim 1, wherein the orifice has a diameter of about between 0.039 inches and 0.045 inches.

15. The method of claim 11, comprising:

monitoring a flow indicator ball in communication with the subglottic tube interface port, wherein the flow indicator ball is visibly held in an elevated position by an airflow from a subglottic tube through the subglottic tube interface port.

16. The method of claim 15, comprising:

configuring the indicator ball to be held in the elevated position when said airflow provides subglottic aspiration.

17. The method of claim 11, comprising:

opening a direct flow channel between the vacuum source port and the subglottic tube interface port;

wherein the direct flow channel is normally closed by actuating a momentary actuator in communication with the direct flow channel, the momentary actuator configured to open the direct flow channel causing flow to bypass the regulator module in response to a momentary manipulation by a user for clearing blockages affecting the subglottic tube interface port.

18. The method of claim 17, wherein the momentary actuator comprises a spring biased push button valve.

19. The method of claim 11 comprising, connecting the vacuum supply port of the regulator apparatus to a standard medical vacuum regulator in communication with the facility vacuum supply, the standard vacuum regulator being concurrently accessible for use by other vacuum devices.

20. The method of claim 19, comprising, periodically clearing the subglottic tube interface port by actuating the momentary actuator.

21. A subglottic tube vacuum regulator, comprising:

an internal vacuum flow channel;

a vacuum source port in communication with the internal vacuum flow channel;

a subglottic tube interface port in communication with the internal vacuum flow channel;

a bleed orifice in the internal vacuum flow channel to provide increased flow through the subglottic tube interface port for a reduced vacuum in the internal vacuum flow channel; and wherein airflow at the vacuum source port is in a direction opposite to airflow at the bleed orifice.

22. The subglottic tube vacuum regulator of claim 21, comprising:

a flow indicator ball in communication with the subglottic tube interface port, wherein the flow indicator ball is configured to be visibly held in an elevated position by airflow through the subglottic tube interface port.

* * * * *